(12) United States Patent
Schönberger

(10) Patent No.: US 9,440,996 B2
(45) Date of Patent: Sep. 13, 2016

(54) ALPHA-ALKOXYSILANE-TERMINATED PREPOLYMER FOR FAST-CURING SPRAY FOAMS WITH IMPROVED PROPELLANT GAS SOLUBILITY

(71) Applicant: BAYER INTELLECTUAL PROPERTY GMBH, Monheim (DE)

(72) Inventor: Jan Schönberger, Haan (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 14/348,253

(22) PCT Filed: Sep. 25, 2012

(86) PCT No.: PCT/EP2012/068833
§ 371 (c)(1),
(2) Date: Mar. 28, 2014

(87) PCT Pub. No.: WO2013/045422
PCT Pub. Date: Apr. 4, 2013

(65) Prior Publication Data
US 2014/0255373 A1 Sep. 11, 2014

(30) Foreign Application Priority Data

Sep. 29, 2011 (EP) .................................... 11183214

(51) Int. Cl.
| | |
|---|---|
| *C08G 18/10* | (2006.01) |
| *C07F 7/10* | (2006.01) |
| *C08G 18/48* | (2006.01) |
| *A61L 26/00* | (2006.01) |
| *A61L 15/26* | (2006.01) |
| *A61L 15/42* | (2006.01) |
| *B65D 83/14* | (2006.01) |
| *C08G 18/02* | (2006.01) |
| *C08G 101/00* | (2006.01) |

(52) U.S. Cl.
CPC .................. *C07F 7/10* (2013.01); *A61L 15/26* (2013.01); *A61L 15/425* (2013.01); *A61L 26/0076* (2013.01); *B65D 83/752* (2013.01); *C08G 18/02* (2013.01); *C08G 18/10* (2013.01); *C08G 18/4825* (2013.01); *C08G 18/4837* (2013.01); *C08G 2101/0091* (2013.01)

(58) Field of Classification Search
CPC ............ C08G 18/289; C08G 65/2639; C08G 18/4837; C08G 18/73; C08G 18/4238; C08G 18/10; C08G 18/4833; C08G 2101/0008; C08G 2150/50; C08L 83/04; A61L 15/425; A61L 15/26
See application file for complete search history.

(56) References Cited

U.S. PATENT DOCUMENTS

| | | | |
|---|---|---|---|
| 5,756,751 A | 5/1998 | Schmalstieg et al. | |
| 6,020,389 A | 2/2000 | Hoheneder | |
| 6,054,499 A | 4/2000 | Pauls et al. | |
| 2004/0072921 A1 | 4/2004 | Stanjek et al. | |
| 2004/0204539 A1* | 10/2004 | Schindler et al. | 524/588 |
| 2006/0084711 A1 | 4/2006 | Stanjek et al. | |
| 2007/0167598 A1* | 7/2007 | Stanjek et al. | 528/25 |
| 2009/0018480 A1 | 1/2009 | Mager et al. | |
| 2013/0161352 A1 | 6/2013 | Bodet et al. | |
| 2013/0168413 A1 | 7/2013 | Bodet et al. | |

FOREIGN PATENT DOCUMENTS

| | | |
|---|---|---|
| DE | 4303848 A1 | 8/1994 |
| EP | 0807649 A1 | 11/1997 |
| EP | 1829908 A1 | 9/2007 |
| EP | 2014314 A1 | 1/2009 |
| WO | WO-00/04069 A1 | 1/2000 |
| WO | WO-02/066532 A1 | 8/2002 |
| WO | WO-2004104078 A1 | 12/2004 |
| WO | PCT/EP2011/063909 | 2/2012 |
| WO | PCT/EP2011/063910 | 2/2012 |
| WO | WO-2012022685 A1 | 2/2012 |
| WO | WO-2012022686 A1 | 2/2012 |

OTHER PUBLICATIONS

Poggenklas, Barbara, et al., "Silane-Crosslinking High-Performance Spray Foams", Organosilicon Chemistry VI: Molecles to Materials, (2003), pp. 813-817.
International Search Report for PCT/EP2012/068833 mailed Nov. 23, 2012.

\* cited by examiner

*Primary Examiner* — John Cooney
(74) *Attorney, Agent, or Firm* — Drinker Biddle & Reath LLP

(57) ABSTRACT

The present invention relates to an alpha-alkoxysilane-terminated prepolymer preparable by reaction of at least one polyether polyol, of a polyisocyanate and of an alpha-alkoxysilane having at least one isocyanate-reactive group, said polyether polyol having a weight average of 500 to 7000 g/mol and having ethylene oxide and propylene oxide units, the proportion of ethylene oxide units being up to 50% by weight based on the polyether polyol. The invention further provides a process for preparing an inventive alpha-alkoxysilane-terminated prepolymer, a composition, a multicomponent system and a spray can comprising an inventive alpha-alkoxysilane-terminated prepolymer, and also a moulding obtainable by polymerization from an inventive alpha-alkoxysilane-terminated prepolymer.

19 Claims, No Drawings

ALPHA-ALKOXYSILANE-TERMINATED PREPOLYMER FOR FAST-CURING SPRAY FOAMS WITH IMPROVED PROPELLANT GAS SOLUBILITY

CROSS-REFERENCE TO RELATED APPLICATIONS

This application is a national stage application (under 35 U.S.C. §371) of PCT/EP2012/068833, filed Sep. 25, 2012, which claims benefit of European application 11183214.3, filed Sep. 29, 2011.

The present invention relates to an α-alkoxysilane-terminated prepolymer obtainable by reaction of at least a polyether polyol, a polyisocyanate and an α-alkoxysilane having at least one isocyanate-reactive group. The present invention further relates to a process for preparing an α-alkoxysilane-terminated prepolymer of the present invention, to a composition, to a multicomponent system and to a pressurized can containing an α-alkoxysilane-terminated prepolymer of the present invention and also to a shaped article obtainable by polymerizing an α-alkoxysilane-terminated prepolymer of the present invention.

Sprayable compositions are known from the prior art. There are, for instance, sprayable in-situ foams for filling cavities, for example in the building construction sector. They find particular application in the filling of gaps and voids between frames of windows and doors and the surrounding brickwork, and are notable for good damp-proofing properties as well as good thermal insulation properties. Sprayable compositions of this type are further used to insulate pipework lines or to fill cavities in technical equipment.

These aforementioned in-situ foams are typically polyurethane (PU) foams. These foams are based on compositions which consist of uncrosslinked prepolymers having a large number of free isocyanate groups. Free isocyanate groups are very reactive in that normal ambient temperature is sufficient to cause them to react with each other in the presence of water/moisture to construct a polymeric network from the prepolymers. Alcohols having two or more OH groups, corresponding thiols and also primary or secondary amines and mixtures thereof are also possible co-reactants for the above-identified isocyanates as well as the atmospheric humidity. Polyols are particularly common for this use. The reaction with polyols/water gives rise to urethane/urea units which can form hydrogen bonds and so are able to form partly crystalline structures in the cured foam. Foam hardness, compressive strength and tensile strength are all enhanced as a result.

The compositions are frequently put into pressurized cans and are provided with a propellant to facilitate the foaming up of the prepolymers as they exit from the pressurized can. In addition, the isocyanate groups of the prepolymer react with the atmospheric humidity to evolve carbon dioxide which likewise contributes to the foaming. In this reaction, the isocyanate groups involved are converted into amines which in turn can react with further isocyanate groups to form a polymeric network, i.e. are not lost from the crosslinking reaction.

Polyurethane compositions can be manufactured as 1K foams or else as two-component (2K) foams. While 1K foams need the influence of atmospheric humidity for curing, 2K foams involve separate storage of a polyisocyanate and of a polyol and their mixing with each other only immediately before discharge. This mixing process takes place, for example, in the pressurized body of the pressurized can, the contents of which then have to be fully used up speedily, since the polymerization takes place irrespective of whether the foam is or is not discharged. Systems of this type are therefore frequently also referred to as 1.5K foams.

Another possibility is to use a two-chamber pressurized can, where the two components are only mixed with each other in the region of the outlet valve. The main advantage of 2K foams over 1K foams consists in the appreciably faster curing reaction, since it takes place even in the absence of atmospheric humidity. By contrast, the curing rate with 1K foams is determined by the atmospheric humidity and also by the rate at which the atmospheric humidity diffuses into the foamed material.

The aforementioned compositions, in addition to the prepolymer components, typically contain still further, auxiliary materials, for example foam stabilizers and also catalysts to hasten the crosslinking reaction. The catalysts used are primarily organotin or organotitanium compounds, for example dibutyltin dilaurate.

The above-identified polyurethane foams have good mechanical and thermally insulating properties in the cured state and very good adherence to most adherends.

However, the above-identified polyurethane foams can still contain monomeric diisocyanates, which is undesirable if the foams are to be used for treatment of wounds.

To reduce the hazard potential associated with the spray foams referred to above, DE 43 03 848 A1 describes prepolymers containing at most only minimal concentrations of monomeric isocyanates, if any. Yet there is still a certain risk that the prepolymer may still have free isocyanate groups, which is again undesirable for medical applications.

Polymerizable foamable compositions which do not cure via free isocyanate groups have been developed in recent years for the aforementioned reasons. U.S. Pat. No. 6,020,389 A1, for instance, discloses silicone foams comprising alkoxy-, acyloxy- or oximo-terminated silicone prepolymers. These compounds polymerize via a condensation reaction of siloxane groups. These compounds are disadvantageous because of their long curing time, since they—like the 1K polyurethane spray foams—are reliant on atmospheric humidity for the polymerization reaction. Full reaction accordingly takes a long time with comparatively thick foamed layers in particular. This is not just inconvenient, but also problematic in that the foam structure formed by the spraying will partly collapse again before the pore walls can have developed sufficient strength of their own due to the ongoing polymerization reaction.

WO 00/04069 discloses alkoxysilane-terminated polyurethane prepolymers. These prepolymers have a conventional polyurethane backbone, which is obtained in a conventional manner by reaction of difunctional isocyanates with polyols. An excess of polyfunctional isocyanates is used to ensure that the respective end groups of the prepolymer chains have free isocyanate groups. These isocyanate-terminated prepolymers are then reacted in a further reaction step with an aminoalkyltrialkoxysilane to form the desired alkoxysilane-terminated polyurethane prepolymers. Aminopropyltrimethoxysilane is used for this in particular. The prepolymer obtained therefrom bears trimethoxysilane-terminated end groups coupled to the polyurethane backbone via a propylene spacer. Owing to the propylene group between the silicon atom and the polyurethane backbone, silanes of this type are also referred to as γ-silanes.

In the curing reaction, γ-silanes react with water to eliminate alcohol and thereby form Si—O—Si networks, curing the prepolymer. Even if γ-silanes are safer than the isocyanate-terminated polyurethane prepolymers from a toxicological viewpoint, they nevertheless have the disadvantage that the curing reaction is comparatively slow. This disadvantage can only be partly compensated by adding large amounts of crosslinking catalysts, including for example the dibutyltin dilaurate also used for polyurethane prepolymers, to γ-silane-based compositions. However, this has a disadvantageous effect on the shelf-life of such compositions in some instances.

Since even comparatively large amounts of crosslinking catalyst cannot fully compensate the low reactivity of γ-silanes, more reactive types of compounds have been sought. They are known, for example, from WO 02/066532 A1. The prepolymers described therein are again silane-terminated polyurethane prepolymers. The essential difference from the previously described γ-silanes is that there is a methylene spacer between the polyurethane backbone and the silicon atom instead of the propylene group. This is why these silanes are also referred to as α-silanes. The shorter distance from the silicon atom to the highly polar urea group of the polyurethane backbone increases the reactivity of the alkoxy groups on the silicon atom (α-effect), so the hydrolysis of the alkoxysilane groups and the subsequent condensation reaction proceeds at an appreciably increased rate.

The disadvantage with both α-silanes and γ-silanes is, however, that it is extremely tricky to use these prepolymers for the manufacture of sprayable foams. Especially the problem of providing a cannable spray foam that is to be capable of generating a loose porous structure of large porous volume is scarcely tractable. The reason for this is that, unlike polyurethane foams, the crosslinking reaction in the presence of water does not give rise to gaseous reaction products (like $CO_2$ with polyurethane foam), but leads to the elimination of alcohols, for example methanol or ethanol. These compounds, unlike a gaseous reaction product, are incapable of developing frothing effects, so a foam sprayed out of a pressurized can will tend to collapse in on itself until cured. This effect is very difficult to control even through use of foam stabilizers.

This problem is addressed by EP 1 829 908 A1, which proposes a 2K silane prepolymer-based system. The first component here utilizes the silane prepolymer, for example a silane-terminated polyurethane prepolymer, dibutyltin dilaurate as catalyst and also major amounts of calcium carbonate. The second component consists of a highly concentrated aqueous citric acid solution. To generate this 2K foam, the two components are mixed together and exported to the desired spot via a spray applicator. In the process, the water in the second component effectuates the crosslinking reaction of the silane prepolymer, while the calcium carbonate comes under the effect of the highly concentrated citric acid solution and releases $CO_2$. The carbon dioxide has the effect, which is familiar from polyurethane prepolymers, of frothing the exported prepolymer mixture.

However, this system is disadvantageous in that the highly concentrated citric acid solution has a pH of about 1-2 and so displays caustic or at least irritant properties. Aerosol formation, which may occur with aerosol spray cans in particular, irritates the eyes, the skin and particularly also the respiratory tract of the user. Moreover, the caustic/corrosive potential of citric acid places an appreciable constraint on where the compositions can be used. For instance, it is completely out of the question to apply such compositions in the medical sector directly to the skin, especially a skin lesion or an injured part of the body, as a sprayable wound dressing.

A further known problem with spraying silane-crosslinking foams is that cracks can appear in the fabric of the foam as it undergoes curing. According to the publication "Silane-Crosslinking High-Performance Spray Foams, Barbara Poggenklas, Heinrich Sommer, Volker Stanjek, Richard Weidner, Johann Weis, Organosilicon Chemistry VI: From Molecules to Materials, [European Silicon Days], Munich, DE, 11-12 Sep. 2003" the cracking was attributable to excessively rapid diffusion of the propellant gas out of the still fresh silane foam. A less polar propellant gas, such as propane/butane, was more suitable for a reduced rate of diffusion, but it was only sparingly soluble in the known silane-terminated prepolymers. Insufficient propellant gas solubility also had a disadvantageous effect on the foaming behavior. To address this problem, this publication proposes that long alkyl chains, i.e., apolar groups, be incorporated in from 5 to 10% of the end groups of the α-silane-terminated prepolymers in order that the solubility of the apolar propellant in the polymer may be improved. However, no specific particulars are provided as to which solubilities for apolar propellant gas are achievable by this measure. In any event, the insertion of long alkyl chains may cause unwelcome changes in the properties of the silane-terminated prepolymers and the foams obtainable therefrom, for example a distinct increase in foam hardness. This is undesirable in some fields of use.

WO 04/104078 A1 likewise addresses the above-described problem of cracking in silane-crosslinkable spray foams and the associated limited solubility of apolar propellant gases in α-silane-terminated prepolymers. Again, to improve the solubility of apolar propellant gases, it is proposed that 5 to 10% of the end groups of the α-silane-terminated prepolymers be modified with long alkyl chains. This, as mentioned, may cause unwelcome changes in the properties of the prepolymers and of foams resulting therefrom. The α-silane-terminated prepolymers are constructed using short-chain polyether polyols having a molar mass <450 g/mol. The use of such polyols leads to hard foams, which can only be used for a greatly limited range of applications.

Against this background, the present invention has for its object to provide an α-alkoxysilane-terminated prepolymer whence it is possible to produce spray foams which cure rapidly, have a highly porous structure with a high pore volume and also have generally good mechanical properties. The prepolymer or to be more precise a spray foam obtainable therefrom shall further cover a comparatively broad field of use.

This object is achieved by an α-alkoxysilane-terminated prepolymer of the type referred to in the introduction, wherein the polyether polyol has a weight average of 500 to 7000 g/mol, comprises propylene oxide units and has a 0 to 50 wt % fraction, based on the polyether polyol, of ethylene oxide units. Such a prepolymer is particularly suitable for use in isocyanate-free foamable composition which are in turn specifically useful for medical applications such as foamable wound dressings.

A preferred embodiment of the invention comprises an α-alkoxysilane-terminated prepolymer of the type referred to at the beginning wherein the polyether polyol has a weight average of 500 to 7000 g/mol and ethylene oxide as well as propylene oxide units, the proportion of ethylene oxide units being up to 50 wt %, based on the polyether polyol.

The invention provides that the α-alkoxysilane-terminated prepolymer has α-silane groups. This is to be understood as meaning that the prepolymers contain an arithmetic average of at least one α-silane group per prepolymer molecule. However, it can be similarly provided that the alkoxysilane-terminated prepolymer in the composition of the present invention contains exclusively α-silane groups.

An α-silane group, as already explained above, has a methylene spacer between the silicone atom and the polymer backbone. α-Silanes are notable for particularly good reactivity in relation to the condensation reaction. This is why complete disavowal of the use of heavy metal-based cross-linking catalysts such as organic titanates or organic tin(IV) compounds is possible in the context of the present invention. This is particularly advantageous in relation to medical applications for the composition of the present invention.

Isocyanate-reactive groups are functional groups capable of reacting with isocyanate groups by hydrogen elimination. The isocyanate-reactive groups are preferably OH, SH and/or amine groups.

It surprisingly transpired that the α-alkoxysilane-terminated prepolymer of the aforementioned type is highly soluble to apolar propellants, such as alkanes or alkenes, particularly the industrially significant mixtures of propane/butane. These prepolymers can accordingly be made available as can-pressurizable 1K or 2K reactive foam compositions. These can be expanded into fine-cell and strongly porous foams in that the 1K foam compositions cure via the action of atmospheric humidity, while the 2K foam compositions contain a curative component—most simply, a protic solvent such as water or an alcohol—and are made to polymerize in this way.

2K foam compositions of this type can be filled into a pressurized can having two or more chambers, and can be foamed up by means of propellant gases. In a pressurized can of this type, the two components of the composition according to the present invention are separated from each other until directly before the moment of foaming, requiring a long shelf-life even without the addition of water traps or other stabilizers. As the 2K composition discharges from the pressurized can, its mixing advantageously takes place in the vicinity of the outlet valve. The resulting mixture formed from the first and second components is caused by the propellant gas also contained therein to foam up immediately on leaving the pressurized can.

The α-alkoxysilane-terminated prepolymer of the present invention can suitably be prepared using in principle any aromatic, araliphatic, aliphatic or cycloaliphatic polyisocyanate having an NCO functionality of ≥2 which is known per se to a person skilled in the art. Examples of this type of polyisocyanates are 1,4-butylene diisocyanate, 1,6-hexamethylene diisocyanate (HDI), isophorone diisocyanate (IPDI), 2,2,4- and/or 2,4,4-trimethylhexamethylene diisocyanate, the isomeric bis(4,4'-isocyanato-cyclohexyl)methanes or their mixtures of any desired isomeric content, 1,4-cyclohexylene diisocyanate, 1,4-phenylene diisocyanate, 2,4- and/or 2,6-tolylene diisocyanate, 1,5-naphthylene diisocyanate, 2,2'- and/or 2,4'- and/or 4,4'-diphenylmethane diisocyanate, 1,3- and/or 1,4-bis(2-isocyanatoprop-2-yl)benzene (TMXDI), 1,3-bis(isocyanato-methyl)benzene (XDI), alkyl 2,6-diisocyanatohexanoate (lysine diisocyanates) with C1-C8 alkyl groups, and also 4-isocyanatomethyl-1,8-octane diisocyanate (nonane triisocyanate) and triphenylmethane 4,4',4"-triisocyanate.

In addition to the polyisocyanates referred to above, modified diisocyanates or triisocyanates of uretdione, isocyanurate, urethane, allophanate, biuret, iminooxadiazinedione and/or oxadiazinetrione structure can also be used proportionately.

Preference is given to polyisocyanates or polyisocyanate mixtures of the aforementioned type with exclusively aliphatically and/or cycloaliphatically bound isocyanate groups and an average NCO functionality of 2 to 4, preferably 2 to 2.6 and more preferably 2 to 2.4 for the mixture.

Polyether polyols useful according to the present invention include, for example, the polytetramethylene glycol polyethers which are known per se in polyurethane chemistry, which are obtainable for example by polymerization of tetrahydrofuran via cationic ring opening. Likewise suitable are the familiar addition products of styrene oxide, ethylene oxide, propylene oxide, butylene oxides, and/or epichlorohydrin on to di- or polyfunctional starter molecules. Useful starter molecules include any of the compounds known to be useful in the prior art, for example water, butyldiglycol, glycerol, diethylene glycol, trimethyolpropane, propylene glycol, sorbitol, ethylenediamine, triethanolamine, 1,4-butanediol. Preferred starter molecules are water, ethylene glycol, propylene glycol, 1,4-butanediol, diethylene glycol and butyldiglycol.

In further refinement of the α-alkoxysilane-terminated prepolymer according to the present invention, the fraction of ethylene oxide units is not more than 30 wt % and further preferably not more than 20 wt %, based on the polyether polyol. More preferably, the proportion of ethylene oxide units is from 3 to 30 wt %, especially 5 to 20 wt %, each based on the polyether polyol. The other alkylene oxide units may very largely be propylene oxide units, but other structural units may also be present. Prepolymers having such a structure combine a particularly good propellant gas solubility in respect of alkanes with good flexibility on the part of the foams obtained.

Advantageously, however, the proportion of ethylene oxide units in the polyether is not to be set too high, since this would otherwise lead to severe swelling of the wound dressing. Moreover, propellant gas solubility decreases with increasing ethylene oxide content. Hence a preferred embodiment of the α-alkoxysilane-terminated prepolymer according to the present invention is defined by a proportion of ethylene oxide units which is within the aforementioned ranges. The lower limit of ethylene oxide groups can be located at about 5 wt %, for example. In any event polyethers without ethylene oxide units can also be used.

In a further embodiment of the α-alkoxysilane-terminated prepolymer according to the present invention, the weight average of the polyether polyol is in the range from 800 to 6000 g/mol and more particularly in the range from 1000 to 4500 g/mol. Such prepolymers are likewise notable for good propellant gas solubility in respect of the alkanes mentioned whilst at the same time enabling flexible tuning of the foam hardness to the desired requirements. Comparatively short-chain prepolymers here generally deliver harder foams than long-chain prepolymers.

It is accordingly advantageous for the aforementioned medical applications in particular that the hardness of the polymer foam obtained can be varied via the selection of the chemical nature and/or the chain length for the polymer backbone of the α-alkoxysilane-terminated prepolymer. In addition to the aforementioned parameters, the hardness of the foam can also be modified via further measures, for example via the degree of crosslinking. It is thus possible to form very soft and hence compliant polymer foams or else firm polymer foams which offer support. Medical use is accordingly not restricted to direct wound treatment; instead the immobilization of extremities, for example in the event of bone fractures, ligament strains, sprains etc., is also possible. Applications in the cosmetic sector are likewise conceivable.

In a further preferred embodiment of the invention, the α-alkoxysilane-terminated prepolymer is obtainable by reacting the α-alkoxysilane with an NCO-terminated polyurethane prepolymer, the NCO-terminated polyurethane prepolymer being obtainable by reacting the polyisocyanate with the polyether polyol. The average NCO functionality of the NCO-terminated polyurethane prepolymer may preferably be 4 or less and in particular in the range from 2 to 4. It is likewise preferable in this case for the NCO-terminated polyurethane prepolymer to have a dynamic viscosity at 23° C. of 200 to 10 000 mPas and in particular from 1500 to 4500 mPas.

Viscosity can be conveniently determined using rotary viscometry in accordance with German standard specification DIN 53019 at 23° C. with a rotary viscometer at a rotary frequency of 18 $s^{-1}$ from Anton Paar Germany GmbH, Ostfildern, DE.

An α-alkoxysilane-terminated prepolymer of the aforementioned type is particularly advantageous for medical applications because its viscosity is sufficiently low for it to be easily foamable.

In further preferred manner, the α-silane groups of the α-alkoxysilane-terminated prepolymer according to the present invention are triethoxy-α-silane groups. This is advantageous because comparatively innocuous ethanol is released during the crosslinking reaction, instead of the methanol which is released from the frequently used trimethoxy-α-silanes. Even though the reactivity and hence cure rate of the trimethoxy-α-silanes is higher than that of the triethoxy-α-silanes, the reactivity of the triethoxy-α-silanes is sufficiently high for most applications. Especially when the composition is mixed with a protic solvent such as water, before application, the cure of the alkoxysilane-terminated prepolymer will generally be complete within a few minutes, in some instances even after less than one minute.

It is likewise preferable for the α-silane groups of the alkoxysilane-terminated prepolymer used to be diethoxy-α-silane groups.

The present invention accordingly further provides a process for preparing an α-alkoxysilane-terminated prepolymer according to the present invention, comprising the steps of:
reacting the polyether polyol with the polyisocyanate to form an NCO-terminated polyurethane prepolymer, and
reacting the NCO-terminated polyurethane prepolymer with the α-alkoxysilane to form the α-alkoxysilane-terminated prepolymer.

The invention still further provides an isocyanate-free, foamable composition, in particular for medical applications such as foamable wound dressings, which contains an α-alkoxysilane-terminated prepolymer according to the present invention.

Isocyanate-free herein refers to a system which contains less than 0.5 wt % of isocyanate-containing components.

The composition of the present invention has a high rate of cure. As a result, the mixture can form a self-supporting foam structure more or less immediately after expansion of the mixture, so it is virtually impossible for the foam to collapse before it is fully cured through, which generally takes only a few minutes. In other words, the present invention, in addition to the 1K system, also provides a usable 2K silane foam system whence polymer foams having a high pore volume are obtainable without requiring the additional use of gas-evolving reactants, such as the combination of calcium carbonate and citric acid for example.

In addition to the improved propellant gas solubility, the composition according to the invention has a further advantage in that it has a polymer backbone constructed of EO-PO units, and hence has a homogeneous construction. The compositions according to the present invention can accordingly be used to produce distinctly more flexible foams by comparison with the prior art silane polymers having apolar side chains, which in principle have the construction of a block copolymer/terpolymer.

The composition's freedom from isocyanate can be achieved in various possible ways known per se to a person skilled in the art. A particularly suitable option according to the present invention is to purify the prepolymers via a thin-film distillation. This purification procedure is particularly advantageous because it has transpired that compositions whose prepolymers were freed of polyisocyanates via a thin-film distillation have better foaming characteristics, since the viscosities of the compositions are simpler to adjust and altogether less viscous prepolymers are obtained. The thin-film distillation in the case of prepolymers having a polyether backbone and polyisocyanate units attached thereto, for example, can take place after the reaction of the polyether polyol with the polyisocyanate, i.e., before the silane group(s) are attached to this intermediate.

The composition according to the present invention is usable for a multiplicity of applications. For instance, it is useful for all application domains in which the prior art above-identified polyurethane foams and also α-/γ-silane foams are proposed, i.e., for the building construction sector, to insulate pipework lines or else to fill cavities in machines.

It has been determined that, surprisingly, in addition to these purposes, the compositions of the present invention are also open to applications in the medical sector, since there is no need to use toxic or irritant compounds.

The medical field of use includes the provision of in situ preparable wound dressings for example. For this, the composition of the present invention can be sprayed, or otherwise applied, as a 1K or 2K foam system of the above-identified kind on to skin injuries or injuries of some other kind. The foamed compositions exhibit no marked adherence to organic tissue such as wound tissue for example, while their porous structure enables them to absorb wound secretions or blood. The reason for this appears to be that the compositions of the present invention, when spray-dispensed under the aforementioned conditions, form an open porous structure, to some extent at least, and hence are absorbent.

The polarity of the compositions according to the present invention and of the foams obtainable therefrom is also advantageous for this purpose, especially in comparison with the prior art silane polymers having apolar side-chains. Thus, the hydrophilicity of the foam obtained can be modified as required, for example to exhibit better absorbance for aqueous fluids, such as blood or wound secretions, via the choice of polyether or to be more precise its polarity.

Even though providing the composition of the present invention in pressurized cans is a convenient option, however, the invention is not limited thereto. Thus, the composition of the present invention is also readily usable in the form of a casting compound which is curable either in the air or on prior mixing with a protic solvent, such as water.

However, the composition according to the present invention is particularly suitable for foam application from a pressurized can. Therefore, the composition preferably contains a pressure-liquefied propellant gas. The propellant gas may preferably comprise at least one alkane or alkene each of 1 to 5 carbon atoms and more particularly at least one compound from the group ethane, propane, n-butane, isobutane, pentane and also mixtures thereof. Although other propellant gases, such as dimethyl ether for example, are also possible in principle, the propellant gases used recruit more preferably from the aforementioned alkanes/alkenes. In addition to the abovementioned good solubility of these propellant gases in the composition of the present invention, they—unlike dimethyl ether—cause on contact with open wounds a less burning sensation in the patient.

The composition at a pressure of 1.5 bar and at a temperature of 20° C., for example, can contain at least 3 wt % of propellant gases, based on the composition, while the propellant gas is completely dissolved in the composition. Complete solubility can be ascertained at 20° C. in "test glasses for optical checks of aerosols" from Pamasol Willi Mäder AG, CH. There is complete solubility for the purposes of the present invention when the propellant gas does not form a visually perceivable second phase for a sustained period (>1 h).

In a particularly preferred embodiment, the content level of dissolved propellant gas is from 10 to 30 wt %, based on the composition, preferably from 15 to 30 wt %.

The present invention further provides an isocyanate-free multicomponent system, in particular for producing foams for medical products such as wound dressings having at least two separate components, wherein the first component comprises a composition as claimed in any of claims 10 to 12 and the second component comprises a protic compound, preferably a protic solvent, in particular an aqueous component.

The second component may most simply be an aqueous component or even consist of water. Advantageously, however, the aqueous component does contain further constituents. It is thus particularly advantageous for it to have a pH of about pH 4.0 to 9.5. This is because it has surprisingly transpired that an α-alkoxysilane-terminated prepolymer is very quickly curable with an aqueous component at the aforementioned pH values, so that a composition of this type can be filled into a two-chamber or multi-chamber pressurized can and be foamed with propellant gases into stable and fine-cell foams. Owing to the moderate pH range of the aqueous component, of about pH 4.0 to 9.5, the composition of the present invention can also be for example applied directly to the human or animal skin.

To further improve skin compatibility, the pH of the aqueous component may preferably be in the range from 4.5 to 8.0, in particular from 5.0 to 6.5. In this pH range there is a virtually complete absence of skin irritation even in the case of sensitive skin. At the same time, the compositions obtained on mixing the first and second components cure at the aforementioned high rate.

The aforementioned pH ranges can in principle be established in any conceivable manner. Thus, the aqueous component may comprise at least an acid, a base or a buffering system, in which case the addition of a buffering system is preferred. For instance, the comparison of two compositions, of which one comprises an acid in the aqueous component and the other comprises a buffering system at the same pH in the aqueous component, shows that the compositions comprising the buffering system have a positive influence on the curing of the silane-terminated prepolymer in that they form finer-cell foams in particular.

Useful acids include organic and inorganic compounds which are at least partly water-soluble and, on dissolving, shift the pH into the acidic region. Mineral acids such as hydrochloric acid, hydrobromic acid, sulfuric acid, nitric acid or phosphoric acid, to name but a few, are examples of this. Useful organic acids include for example formic acid, acetic acid, various α-chloroacetic acids, lactic acid, malic acid, citric acid, tartaric acid, succinic acid and the like. Mixtures of the aforementioned chemistries can also be used.

Bases useful for the purposes of the present invention can likewise be of organic and inorganic origin and at least partly water-soluble, shifting the pH into the alkaline region on dissolving. Examples of these are the alkali metal or alkaline earth metal hydroxides such as sodium hydroxide or potassium hydroxide and ammonia, to name but a few. Useful organic bases include for example nitrogenous compounds such as primary, secondary, tertiary aliphatic or cycloaliphatic amines and also aromatic amines. Specifically methylamine, dimethylamine, trimethylamine, ethylamine, methyldiethanolamine (MDEA), piperidine and pyridine may be mentioned by way of example only. Mixtures of the aforementioned chemistries can moreover likewise be used.

A buffering system used according to the present invention comprises in general a mixture of a weak acid and its conjugated base, or vice versa. Ampholytes can also be used. Buffers used in the context of the present invention are more particularly selected from acetate buffer, phosphate buffer, carbonate buffer, citrate buffer, tartrate buffer, succinic acid buffer, TRIS, HEPES, HEPPS, MES, Michaelis buffer or mixtures thereof. However, the present invention is not limited to the aforementioned systems. In principle, any buffering system which can be adjusted such that the claimed pH range can be set is usable.

In further refinement of the composition according to the present invention, the concentration of the buffering system is in the range from 0.001 to 2.0 mol/l, in particular from 0.01 to 0.5 mol/l. These concentrations are particularly preferred because on the one hand sufficient buffering capacity is made available while, on the other hand, there is no crystallization of buffer out of the aqueous component under typical storage conditions. This would be disadvantageous for use in pressurized cans for example, since crystallized-out constituents might plug the mixing device or the nozzle of the pressurized can.

Further preferably, the buffering capacity is at least 0.01 mol/l, in particular in the range from 0.02 to 0.1 mol/l.

It may be advantageous in the context of the present invention for the viscosity of the aqueous component to be adjusted, for example in order that its miscibility with the silane-terminated prepolymer in a mixing device of a two-chamber pressurized can may be facilitated. The dynamic viscosity of the aqueous component at 23° C. can thus be in the range from 10 to 4000 mPas, in particular in the range from 300 to 1000 mPas. Viscosity can be conveniently determined using a rotary viscometry in accordance with German standard specification DIN 53019 at 23° C. with a rotary viscometer at a rotary frequency of 18 s$^{-1}$ from Anton Paar Germany GmbH, Ostfildern, DE.

In a particularly preferred refinement of the composition according to the present invention, the aqueous component may include a thickener. A thickener can be used to set the abovementioned viscosities. There is a further advantage to the thickener in that it has some stabilizing effect on the foam and so can help maintain the foam structure until it has reached the point where it is capable of supporting its own weight.

It has further surprisingly transpired that the addition of thickeners, in particular the addition of starch- or cellulose-based thickeners, has the effect that a whole series of commercially available propellant gases become soluble in the aqueous phase. Since the solubility of these propellant gases in the first component, comprising the silane prepolymer, tends to be less problematic, this prevents phase separation between the propellant gas and the first/second component in the respective chambers of the multi-chamber pressurized can. Hence the propellant gas and the first component, on the one hand, and the propellant gas and the second component, on the other, form a very largely homogeneous mixture until the time of emerging from the pressurized can. After the two, first and second components, which are kept apart in the can, have come to be mixed in a mixing nozzle of the pressurized can, the propellant gas dissolved in the mixture causes substantial expansion of this mixture as it emerges from the pressurized can, so a fine-cell foam is obtained. Therefore, thickeners to be used to particular advantage are selected from starch, starch derivatives, dextrin derivatives, polysaccharide derivatives such as guar gum, cellulose, cellulose derivates, in particular cellulose ethers, cellulose esters, organic wholly synthetic thickeners based on polyacrylic acids, polyvinylpyrrolidones, poly(meth)acrylics or polyurethanes (associative thickeners) and also inorganic thickeners, such as bentonites or silicas or mixtures thereof. Specific examples are methylcellulose or carboxymethylcellulose, for example as sodium salt.

It can further be provided in the context of the present invention that the aqueous component comprises or consists of a polyurethane dispersion. A commercially available polyurethane dispersion can be used therefor for example, the concentration of which can also be lowered with additional water, if desired, and which is then brought into the recited pH range using the abovementioned possibilities. The use of a polyurethane dispersion is advantageous because propellant gas solubility in the aqueous phase can be increased in this way with regard to the abovementioned alkanes and alkenes specifically.

A further advantage of the aforementioned pH values in combination with the polyurethane dispersion is that in these ranges there is generally no coagulation of the polymer particles of the polyurethane dispersion; in other words, the dispersion is stable in storage under these conditions. It has surprisingly transpired that the use of a polyurethane dispersion can further increase the solubility of commercially available propellant gases in the aqueous component. It is therefore particularly preferable to use a polyurethane dispersion and a thickener of the aforementioned type.

The polyurethane dispersion used can in principle be any commercially available polyurethane dispersion. However, it is again advantageous here to use polyurethane dispersions prepared from isocyanates free from aromatics, since these are less concerning for medical applications in particular. In addition, the polyurethane dispersion can also contain further ingredients. The polyurethane content of the polyurethane dispersion is more preferably in the range from 5 to 65 wt % and especially in the range from 20 to 60 wt %.

In development of the composition according to the present invention, the weight average of the polyurethane in the polyurethane dispersion is in the range 10 000 to 1 000 000 g/mol, especially 20 000 to 200 000 g/mol, all determined via gel permeation chromatography versus polystyrene standard in tetrahydrofuran at 23° C. Polyurethane dispersions having such molar masses are particularly advantageous because they constitute storage-stable polyurethane dispersions which, moreover, on filling into pressurized cans, bring about good solubility for the propellant gas in the second component.

In a particularly preferred embodiment of the composition according to the present invention, the multicomponent system comprises an active medical and/or cosmetic ingredient. In the case of the two- or multi-component composition, this active medical and/or cosmetic ingredient can be provided in the first and/or second component. There is no sharp delimitation between the two groups of active ingredients, since many active medical ingredients also have cosmetic effects.

It is likewise conceivable in this context for the active ingredient(s) to be provided in the form of a further, i.e., third or fourth, component and to be mixed with the first and second components only immediately before application of the composition. Owing to the increase in complexity of the composition as a number of separate components increases, however, this route is generally only sensible when the active ingredients used are incompatible not only with the first component but also with the second component.

The active ingredients can be in the form of pure active ingredient or alternatively in encapsulated form in order that, for example, a delayed time of release may be achieved.

Useful active cosmetic ingredients include particularly those having skin-caring properties, for example active moisture-promoting or skin-calming ingredients.

Useful active medical ingredients for the purposes of the present invention include a multiplicity of types and classes of active ingredients.

Such an active medical ingredient may comprise for example a component that releases nitrogen monoxide under in vivo conditions, preferably L-arginine or an L-arginine-containing or an L-arginine-releasing component, more preferably L-arginine hydrochloride. Proline, ornithine and/or other biogenic intermediates such as, for example, biogenic polyamines (spermine, spermitine, putrescine or bioactive artificial polyamines) can also be used. Components of this type are known to augment wound healing, while their continuous substantially uniform rate of release is particularly conducive to wound healing.

Further active ingredients usable according to the present invention comprise at least one substance selected from the group of vitamins or provitamins, carotenoids, analgesics, antiseptics, hemostyptics, antihistamines, antimicrobial metals or salts thereof, plant-based wound healing promoter substances or substance mixtures, plant extracts, enzymes, growth factors, enzyme inhibitors and also combinations thereof.

Suitable analgesics are in particular non-steroidal analgesics, especially salicylic acid, acetylsalicylic acid and its derivatives e.g. Aspirin®, aniline and its derivatives, acetaminophen e.g. Paracetamol®, anthranilic acid and its derivatives e.g. mefenamic acid, pyrazole or its derivatives e.g. methamizole, Novalgin®, phenazone, Antipyrin®, isopropylphenazone and most preferably arylacetic acids and derivatives thereof, heteroarylacetic acids and also derivatives thereof, arylpropionic acids and also derivatives thereof and heteroarylpropionic acids and also derivatives thereof e.g. Indometacin®, Diclofenac®, Ibuprofen®, Naxoprophen®, Indomethacin®, Ketoprofen®, Piroxicam®.

Suitable growth factors include in particular aFGF (Acidic Fibroplast Growth Factor), EGF (Epidermal Growth Factor), PDGF (Platelet Derived Growth Factor), rhPDGF-BB (Becaplermin), PDECGF (Platelet Derived Endothelial Cell Growth Factor), bFGF (Basic Fibroplast Growth Factor), TGF α; (Transforming Growth Factor alpha), TGF β (Transforming Growth Factor beta), KGF (Keratinocyte Growth Factor), IGF1/IGF2 (Insulin-Like Growth Factor) and TNF (Tumor Necrosis Factor).

Suitable vitamins or provitamins are especially the fat-soluble or water-soluble vitamins vitamin A, group of retinoids, provitamin A, group of carotenoids, especially β-carotene, vitamin E, group of tocopherols, especially α-tocopherol, β-tocopherol, γ-tocopherol, δ-tocopherol and α-tocotrienol, β-tocotrienol, γ-tocotrienol and δ-tocotrienol, vitamin K, phylloquinone, especially phytomenadione or plant-based vitamin K, vitamin C, L-ascorbic acid, vitamin B1, thiamine, vitamin B2, riboflavin, vitamin G, vitamin B3, niacin, nicotinic acid and nicotinamide, vitamin B5, pantothenic acid, provitamin B5, panthenol or dexpanthenol, vitamin B6, vitamin B7, vitamin H, biotin, vitamin B9, folic acid and also combinations thereof.

A useful antiseptic is any antiseptic that has a germicidal, bactericidal, bacteriostatic, fungicidal, virucidal, virustatic and/or generally microbiocidal effect.

Antiseptics selected from the group resorcinol, iodine, iodine-povidone, chlorhexidine, benzalkonium chloride, benzoic acid, benzoyl peroxide or cetylpyridinium chloride are suitable in particular. In addition, antimicrobial metals in particular are also useful as antiseptics. Useful antimicrobial metals include in particular silver, copper or zinc and also their salts, oxides or complexes in combination or alone.

Plant-based active wound healing promoter ingredients in the context of the present invention are in particular extracts of chamomile, *hamamelis* extracts e.g. *Hamamelis virgina, Calendula* extract, aloe extract e.g. *Aloe vera, Aloe barbadensis, Aloe feroxoder* or *Aloe vulgaris*, green tea extracts, seaweed extract e.g. red algae or green algae extract, avocado extract, myrrh extract e.g. *Commophora molmol*, bamboo extracts and also combinations thereof.

A particularly preferred embodiment of the composition according to the present invention contains at least an active medical ingredient particularly selected from substances that release nitrogen monoxide under in vivo conditions, and also substance selected from the group of vitamins or provitamins, carotenoids, analgesics, antiseptics, hemostyptics, antihistamines, antimicrobial metals or salts thereof, plant-based wound healing promoter substances or substance mixtures, plant extracts, enzymes, growth factors, enzyme inhibitors and also combinations thereof.

The active-ingredient content depends in principle primarily on the medically required dose and also on the degree of compatibility with the remaining constituents of the composition according to the present invention.

The composition of the present invention may also comprise further, auxiliary substances. Possibilities here include, for example, foam stabilizers, thixotroping agents, thickeners, antioxidants, photoprotectants, emulsifiers, plasticizers, pigments, fillers, pack-stabilizing additives, biocides, cosolvents, and/or flow control agents.

Alkylpolyglycosides for example are useful as foam stabilizers. They are obtainable in a conventional manner known to those skilled in the art by reaction of comparatively long-chain monoalcohols with mono-, di- or polysaccharides (Kirk-Othmer Encyclopedia of Chemical Technology, John Wiley & Sons, Vol. 24, p. 29). The comparatively long-chain monoalcohols, which optionally may also be branched, preferably comprise an alkyl moiety of 4 to 22 carbon atoms, preferably 8 to 18 carbon atoms and more preferably 10 to 12 carbon atoms. Specific examples of comparatively long-chain monoalcohols are 1-butanol, 1-propanol, 1-hexanol, 1-octanol, 2-ethylhexanol, 1-decanol, 1-undecanol, 1-dodecanol (lauryl alcohol), 1-tetradecanol (myristyl alcohol) and 1-octadecanol (stearyl alcohol). It will be appreciated that mixtures of the comparatively long-chain monoalcohols mentioned can also be used.

These alkylpolyglycosides preferably have structures derived from glucose. Particular preference is given to using alkylpolyglycosides of formula (I).

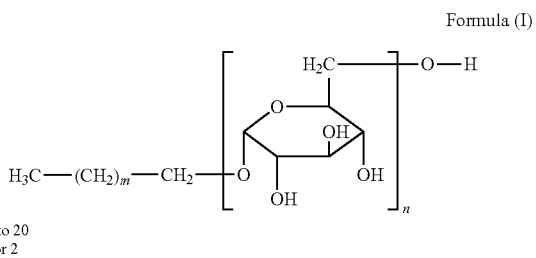

Formula (I)

$m$ = 4 to 20
$n$ = 1 or 2 m is preferably from 6 to 20 and more preferably from 10 to 16.

The alkylpolyglycosides preferably have an HLB value of less than 20, more preferably of less than 16 and most preferably of less than 14, the HLB value being computed using the formula HLB=20·Mh/M, where Mh is the molar mass of the hydrophilic portion of a molecule and M is the molar mass of the entire molecule (Griffin, W. C.: Classification of surface active agents by HLB, J. Soc. Cosmet. Chem. 1, 1949).

Further foam stabilizers include conventional anionic, cationic, amphoteric and nonionic surfactants and also mixtures thereof. Preference is given to using alkylpolyglycosides, EO-PO block copolymers, alkyl or aryl alkoxylates, siloxane alkoxylates, esters of sulfosuccinic acid and/or alkali or alkaline earth metal alkanoates.

Particular preference is given to using EO-PO block copolymers.

In addition, to improve the foam properties of the resulting foam, conventional monohydric and polyhydric alcohols and also mixtures thereof can be used. These are monohydric or polyhydric alcohols or polyols, such as ethanol, propanol, butanol, decanol, tridecanol, hexadecanol, ethylene glycol, neopentyl glycol, butanediol, hexanediol, decanediol, trimethylolpropane, glycerol, pentaerythritol, monofunctional polyether alcohols and polyester alcohols, polyetherdiols and polyesterdiols.

These foam stabilizers can be added to the first component and/or preferably to the second component, provided no chemical reaction takes place with the respective components. The overall content of these compounds, based on the composition of the present invention, is especially in the range from 0.1 to 20 wt % and preferably in the range from 1 to 10 wt %.

The mixing ratios of the first and second components of the two- or multi-component composition according to the present invention are advantageously adjusted relative to each other such that complete polymerization takes place with the first component ideally being converted quantitatively therein. For example, the first and second components of the composition according to the present invention are therefore present therein in a volume ratio of 1:10 to 10:1 relative to each other, preferably in a volume ratio of 1:1 to 5:1 relative to each other, especially 2:1 to 3:1, more preferably at about 2.5:1.

The present invention further provides a shaped article which takes the form of a wound dressing in particular and which is obtainable by complete polymerization of an α-alkoxysilane-terminated prepolymer according to the present invention, a composition according to the present invention or a multicomponent system according to the present invention. In the first case mentioned, the polymerization takes place by action of atmospheric humidity for example. In the case of the multicomponent system, the components are first mixed and then the resulting mixture is subjected to complete polymerization. Complete polymerization of this mixture at room temperature preferably takes not more than five minutes, more preferably not more than three minutes and even more preferably not more than one minute. In the case of the one-component compositions, the time to complete polymerization depends chiefly on the thickness of the exported layer.

Complete polymerization for the purposes of the present invention is to be understood as meaning more than just a skin having been formed on the outside; that is, more than that the outside surface of the shaped article is no longer tacky, but that the prepolymers have very largely undergone complete reaction. This is verified to be the case in the context of the present invention when the shaped article obtained is completely indented for some seconds with the finger and then automatically returns to the original state when the pressure of the finger is removed.

Rapid curing of this kind is advantageous in medical applications in particular, specifically for the use as a sprayable foaming wound dressing. This is because it is only the extremely rapid curing which makes it possible in the first place that the wound dressing can be promptly enclosed in a bandage and put under mechanical loading by the patient. Long waiting times can be avoided as a result.

The invention thus further provides for the use of a specifically foamed reaction product of an α-alkoxysilane-terminated prepolymer according to the present invention, of a composition according to the present invention or of a multicomponent system according to the present invention, as a wound dressing. A wound dressing of this kind has the advantage that the foam structure is not only capable of imbibing wound secretions, but simultaneously also of providing mechanical protection for the wound against knocks and the like. Even the pressure of garments on the wound is partially absorbed by the foam structure.

The sprayed wound dressing further conforms ideally to the usually irregular contours of a wound, thus ensuring a wound covering which is very largely free from pressure pain due to improper wound-dressing fit. In addition, the wound dressing obtained according to the present invention shortens the time needed for wound care compared with care using a traditional wound dressing, since there is no need for the time-consuming cutting to size and shape.

The present invention further provides a pressurized can containing an α-alkoxysilane-terminated prepolymer according to the invention, a composition according to the invention or a multicomponent system according to the invention, wherein the pressurized can is more particularly pressurized with a liquid propellant gas to a pressure of at least 1.5 bar. Useful propellant gases include particularly the pressure-liquefied alkanes and alkenes already more particularly specified above.

Preferably, moreover, the pressurized can need only be filled with sufficient propellant gas to correspond to the solubility of the propellant gas in the composition at fill pressure. The solubility can be determined via the above-described lack of phase separation after one hour.

The pressurized can may be more particularly constructed as a two- or generally as a multi-chamber pressurized can having an outlet valve and a mixing nozzle, in which case the composition according to the present invention is introduced in a first chamber of the two-chamber pressurized can and the second chamber contains an aqueous component or some other protic solvent, wherein the first or both of the chambers contain a liquefied propellant gas under superatmospheric pressure, in particular a pressure of not less than 1.5 bar. The liquefied propellant gas in the two chambers can be the same or different.

A two-chamber pressurized can which is particularly suitable for this purpose is known, for example from the as yet unpublished PCT applications having the application numbers PCT/EP2011/063910 and PCT/EP2011/063909, the content of each of which is fully incorporated herein by reference.

In a further embodiment of the pressurized can according to the present invention, the propellant gases are soluble not only in the first component but also in the second component, the solubility being not less than 3 wt % at a fill pressure of at least 1.5 bar and at a temperature of 20° C. and more particularly the amount of propellant gas introduced being not more than that which corresponds to the solubility. This ensures that the spray-dispensed foam is of consistent quality, since it is never the case that only propellant gas will escape from one of the chambers at the start of the spraying operation and hence the mixing ratio between the first and second components will be nonoptimal. Compositions particularly suitable for this include one of the aforementioned thickeners and/or a polyurethane dispersion in the aqueous component.

There is a further advantage in that, owing to the solubility of the propellant gas in the chambers of the pressurized can, no phase separation comes about between the first/second component and the propellant gas. Therefore, the propellant gas only escapes as the pressurized can is actuated and the first and second components become mixed, and foams up this mixture in the process. The very rapid curing time of the composition according to the present invention has the effect that the foam structure produced by the propellant gas "freezes" and does not collapse in on itself.

The aforementioned effect is amplified by the use of a thickener of the aforementioned kind and/or of a polyurethane dispersion in the aqueous component, since both the thickener and the dispersion to some extent have stabilizing properties on the foam. A propellant gas solubility of not less than 3 wt % is advantageous to ensure sufficient foaming of the exported mixture. The propellant gas content is preferably from 10 to 40 wt % and more preferably from 15 to 25 wt % in the case of the first component and preferably from 3 to 20 wt % and more preferably from 5 to 15 wt % in the case of the second component, all based on the resulting overall weight of the particular mixture. The amount of propellant gas introduced into the can and/or dissolved in the individual components can also be used to influence the foam structure. Thus, a higher quantity of propellant gas in a composition generally leads to a foam of lower density.

The present invention further provides for the use of an α-alkoxysilane-terminated prepolymer according to the present invention, of a composition according to the present invention or of a multicomponent system according to the present invention for production of a foamed or unfoamed shaped polymer article, in particular a sheetlike article such as a wound dressing.

The present invention will now be more particularly elucidated with reference to exemplary embodiments:

EXAMPLES

General

Any amounts, proportions and percentages hereinbelow are based, unless otherwise stated, on the weight and the overall amount, i.e. the overall weight, of the compositions.

Unless stated otherwise, analytical measurements all relate to measurements at temperatures of 23° C.

Methods:

NCO contents, unless expressly mentioned otherwise, were determined volumetrically in accordance with DIN-EN ISO 11909.

The check for free NCO groups was carried out using IR spectroscopy (band at 2260 cm$^{-1}$).

Reported viscosities were determined using rotary viscometry in accordance with German standard specification DIN 53019 at 23° C. with a rotary viscometer at a rotary frequency of 18 s$^{-1}$ from Anton Paar Germany GmbH, Ostfildern, DE.

Storage stability of dispersions was tested over a period of 6 months after production by storage at room temperature.

The maximum soluble propellant gas quantity was determined at 20° C. in "test glasses for optical checks of aerosols" from Pamasol Willi Mäder AG, CH. The maximum soluble propellant gas quantity relates to the weight ratio of propellant gas to the substance/mixture to be investigated, and was reached as soon as the propellant gas just failed to form a second phase on a permanent basis (>1 h).

Since viscosity measurement under propellant gas conditions is technically not feasible, viscosities of STP/propellant gas solutions are estimated on the basis of the flow rate at a 5% gradient in test glasses by comparison with reference solutions of previously determined viscosity (aqueous solutions of different concentrations of Walocel CRT 30 G).

The mixtures were foamed up using a 2K spray apparatus which was filled as described in the as yet unpublished PCT applications having the application numbers PCT/EP2011/063910 and PCT/EP2011/063909.

Employed Substances and Abbreviations:

HDI: hexamethylene 1,6-diisocyanate

Geniosil® XL 926: [(cyclohexylamino)methyl]triethoxysilane (Wacker Chemie AG, Munich, DE)

Walocel CRT 30G: carboxymethylcellulose, sodium salt (Dow Deutschland Anlagengesellschaft mbH, Schwalbach, DE)

P/B 3.5: mixture of propane and isobutane to give a gas pressure of 3.5 bar at 20° C.

The examples which follow demonstrate the preparation of silane-terminated prepolymers.

Example 1

Preparation of Silane-Terminated Prepolymer STP1

A mixture of 800 g of a polyalkylene oxide having a molar mass of 2000 g/mol started on 1,2-propylene glycol and having an ethylene oxide weight fraction of 47% and a propylene oxide weight fraction of 49%, dried beforehand at 80° C. at a pressure of 0.1 mbar for 1 h, and 2.8 g of benzoyl chloride was at 80° C. admixed with 1000 g of HDI, added dropwise in the course of 45 minutes, and subsequently stirred for 2 h. Excess HDI was removed by thin-film distillation at 130° C. and 0.4 mbar to obtain a prepolymer having an NCO content of 3.43% and a viscosity of 1250 mPas.

498 g of the prepolymer obtained were subsequently admixed at 30-40° C. with 104.5 g of Geniosil XL 926 in the course of 15 minutes. Following a further 60 minutes of stirring at 30° C., complete conversion of the NCO prepolymer into the STP was evidenced by IR spectroscopy. The resultant STP dissolved 18% of P/B 3.5 in a storage-stable manner.

Example 2

Preparation of Silane-Terminated Prepolymer STP2

A mixture of 1032 g of a polyalkylene oxide having a molar mass of 4000 g/mol started on 1,2-propylene glycol and having an ethylene oxide weight fraction of 13% and a propylene oxide weight fraction of 86%, dried beforehand at 80° C. at a pressure of 0.1 mbar for 1 h, and 1.8 g of benzoyl chloride was at 80° C. admixed with 650 g of HDI, added dropwise in the course of 30 minutes, and subsequently stirred for 4 h. Excess HDI was removed by thin-film distillation at 130° C. and 0.03 mbar to obtain a prepolymer having an NCO content of 1.82% and a viscosity of 2100 mPas.

207.5 g of the prepolymer obtained were subsequently admixed at 30-40° C. with 24.8 g Geniosil XL 926 in the course of 15 minutes. Following a further 30 minutes of stirring at 30° C., complete conversion of the NCO prepolymer into the STP was evidenced by IR spectroscopy. The resultant STP, which had a viscosity of 9300 mPas, dissolved 28% of P/B 3.5 in a storage-stable manner. The viscosity of this solution was estimated at 400 mPas at 26° C. by comparison.

Example 3

Preparation of Silane-Terminated Prepolymer STP3

A mixture of 201 g of a polyalkylene oxide having a molar mass of 1000 g/mol started on 1,2-propylene glycol and having an ethylene oxide weight fraction of 0% and a propylene oxide weight fraction of 92%, dried beforehand at 80° C. at a pressure of 0.1 mbar for 1 h, and 0.8 g of benzoyl chloride was at 80° C. admixed with 588 g HDI, added dropwise in the course of 30 minutes, and subsequently stirred for 2 h. Excess HDI was removed by thin-film distillation at 140° C. and 0.05 mbar to obtain a prepolymer having an NCO content of 6.09%.

200 g of the prepolymer obtained were subsequently admixed at 30-40° C. with 80 g Geniosil XL 926 in the course of 10 minutes. Following a further 60 minutes of stirring at 30° C., complete conversion of the NCO prepolymer into the STP was evidenced by IR spectroscopy. The resultant STP dissolved 22% of P/B 3.5 in a storage-stable manner.

Example 4

Preparation of Silane-Terminated Prepolymer STP4

A mixture of 270 g of the NCO prepolymer prepared in Example 1 and 1349 g of the NCO prepolymer prepared in Example 2 was admixed at 30-40° C. with 217 g of Geniosil XL 926, added dropwise in the course of 30 minutes, and stirred at 30° C. for a further 30 minutes. Complete conversion of the NCO prepolymer into the STP was evidenced by IR spectroscopy. The resultant STP mixture dissolved 41% of P/B 3.5 or 27% of n-butane in a storage-stable manner.

Example 5

Preparation of Silane-Terminated Prepolymer STP5

A mixture of 423 g of a polyalkylene oxide having a molar mass of 3825 g/mol started on trimethylolpropane and having an ethylene oxide weight fraction of 13% and a propylene oxide weight fraction of 83%, dried beforehand at 80° C. at a pressure of 0.1 mbar for 1 h, and 0.8 g of benzoyl chloride was at 80° C. admixed with 420 g of HDI, added dropwise in the course of 30 minutes, and subsequently stirred for 2 h. Excess HDI was removed by thin-film distillation at 140° C. and 0.05 mbar to obtain a prepolymer having an NCO content of 2.49%.

200 g of the prepolymer obtained were subsequently admixed at 30-40° C. with 37 g of Geniosil XL 926 in the course of 10 minutes. Following a further 60 minutes of stirring at 30° C., complete conversion of the NCO prepolymer into the STP was evidenced by IR spectroscopy. The resultant STP dissolved 37% of isobutane in a storage-stable manner.

Example 6

Preparation of Silane-Terminated Prepolymer STP6

A mixture of 398 g of a polyalkylene oxide having a molar mass of 4800 g/mol started on glycerol and having an ethylene oxide weight fraction of 13% and a propylene oxide weight fraction of 85%, dried beforehand at 80° C. at a pressure of 0.1 mbar for 1 h, and 0.7 g of benzoyl chloride was at 80° C. admixed with 315 g of HDI, added dropwise in the course of 30 minutes, and subsequently stirred for 2 h. Excess HDI was removed by thin-film distillation at 140° C. and 0.05 mbar to obtain a prepolymer having an NCO content of 1.94%.

200 g of the prepolymer obtained were subsequently admixed at 30-40° C. with 28 g Geniosil XL 926 in the course of 10 minutes.

Following a further 60 minutes of stirring at 30° C., complete conversion of the NCO prepolymer into the STP was evidenced by IR spectroscopy. The resultant STP dissolved 39% of P/B 3.5 or 36% of isobutane in a storage-stable manner.

Comparative Example 1

Preparing an STP without Solubility for Alkane Propellant Gases

A mixture of 1000 g HDI and 1 g of benzoyl chloride was at 80° C. admixed with 1000 g of a polyalkylene oxide having a molar mass of 4680 g/mol started on glycerol and having an ethylene oxide weight fraction of 71% and a propylene oxide weight fraction of 26%, dried beforehand at 100° C. at a pressure of 0.1 mbar for 6 h, added dropwise in the course of 3 h, and subsequently stirred for 12 h. Excess HDI was removed by thin-film distillation at 130° C. and 0.1 mbar to obtain a prepolymer having an NCO content of 2.42% and a viscosity of 3500 mPas.

200 g of the prepolymer obtained were subsequently admixed at 30-40° C. with 31.7 g of Geniosil XL 926 in the course of 10 minutes. Following a further 60 minutes of stirring at 30° C., complete conversion of the NCO prepolymer into the STP was evidenced by IR spectroscopy. The resultant STP did not dissolve P/B 3.5.

The tests which follow depict the results of curing tests on the foams. Simultaneous exportation of the two components took place on an MAH 0.5-0.7T static mixer from Adchem GmbH, Wendelstein, DE.

Example 7

Spray Application

All STP/propellant solutions according to the present invention were stable in storage (>2 months) and were easily exported from commercially available spray vessels. The solutions foamed up in the process to form a foam which was stable until fully cured. Similarly, application from a compressed air driven 2K spraying apparatus, wherein the chambers were each filled separately with STP/propellant solution in one of the chambers and with protic liquids such as, for example, water, aqueous acids, aqueous buffering solutions, aqueous catalyst mixtures or alcohols in the second chamber and were exported in a preferred volume ratio of 2.5:1 relative to each other, was accomplished without problems and delivered, within about 5-120 seconds, foams which were stable until the particular STP was fully cured. The foams obtained were soft, fine-cell and useful inter alia as medical wound dressing.

Comparative Example as Per Example 1 of EP 1 829 908

This comparative test is designed to compare the composition of the present invention with the prior art 2K systems, specifically Example 1 of EP 1 829 908. An attempt was made to export component 2 (8 parts of water, 13 parts of citric acid) via the 2K spraying apparatus in synchronicity with STP 1, used according to the present invention, but failed because the mixture already underwent complete curing while still within the static mixer, blocking it completely. Application was accordingly impossible.

Moreover, the 8 parts of water and 13 parts of citric acid making up component 2 mean that the pH of component 2 is about 1, thereby foreclosing pH-sensitive applications such as medical applications, for example, to this system. What is more, this pH represents a potential caustic hazard to the user involved in the event of an application.

The invention claimed is:

1. An α-alkoxysilane-terminated prepolymer obtained by reacting at least a polyether polyol, a polyisocyanate and an α-alkoxysilane, wherein the α-alkoxysilane is [(cyclohexylamino) methyl]triethoxysilane, wherein the polyisocyanate is hexamethylene 1,6-diisocyanate or a polyisocyanate mixture comprising hexamethylene 1,6-diisocyanate, and wherein the polyether polyol has a weight average of 500 to 7000 g/mol, comprises propylene oxide units and has a 0 to 50 wt % fraction, based on the polyether polyol, of ethylene oxide units.

2. The α-alkoxysilane-terminated prepolymer as claimed in claim 1, wherein the fraction of ethylene oxide units is not more than 30 wt % based on the polyether polyol.

3. The α-alkoxysilane-terminated prepolymer as claimed in claim 1, wherein the fraction of ethylene oxide units is not more than 20 wt %, based on the polyether polyol.

4. The α-alkoxysilane-terminated prepolymer as claimed in claim 1, wherein the weight average of the polyether polyol is in the range from 800 to 6000 g/mol.

5. The α-alkoxysilane-terminated prepolymer as claimed in claim 1, wherein the weight average of the polyether polyol is in the range from 1000 to 4500 g/mol.

6. The α-alkoxysilane-terminated prepolymer as claimed in claim 1, wherein the α-alkoxysilane-terminated prepolymer contains triethoxy-α-silane groups.

7. The α-alkoxysilane-terminated prepolymer as claimed in claim 1, wherein the polyisocyanate is an aliphatic polyisocyanate.

8. The α-alkoxysilane-terminated prepolymer as claimed in claim 1, wherein the polymer is obtained by reacting the α-alkoxysilane with an NCO-terminated polyurethane prepolymer, wherein the NCO-terminated polyurethane prepolymer is obtainable by reacting the polyisocyanate with the polyether polyol and the average NCO functionality of the NCO-terminated polyurethane prepolymer is 4 or less.

9. The α-alkoxysilane-terminated prepolymer as claimed in claim 1, wherein the polymer is obtained by reacting the α-alkoxysilane with an NCO-terminated polyurethane prepolymer, wherein the NCO-terminated polyurethane prepolymer is obtainable by reacting the polyisocyanate with the polyether polyol and the average NCO functionality of the NCO-terminated polyurethane prepolymer is in the range from 2 to 4.

10. A process for preparing an α-alkoxysilane-terminated prepolymer as claimed in claim 1, comprising the steps of:
reacting the polyether polyol with the polyisocyanate to form an NCO-terminated polyurethane prepolymer, and
reacting the NCO-terminated polyurethane prepolymer with [(cyclohexylamino) methyl]triethoxysilane to form the α-alkoxysilane-terminated prepolymer.

11. An isocyanate-free, foamable composition wherein the composition contains an α-alkoxysilane-terminated prepolymer as claimed in claim 1.

12. The composition as claimed in claim 11, wherein the composition contains at least an active medical ingredient selected from substances that release nitrogen monoxide under in vivo conditions, or vitamins, provitamins, carotenoids, analgesics, antiseptics, hemostyptics, antihistamines, antimicrobial metals or salts thereof, plant-based wound healing promoter substances or substance mixtures, plant extracts, enzymes, growth factors, enzyme inhibitors and also combinations thereof.

13. The composition as claimed in claim 11, wherein the composition contains a pressure-liquefied propellant gas.

14. The composition as claimed in claim 13, wherein the content level of dissolved propellant gas in the composition is from 10 to 30 wt %.

15. An isocyanate-free multicomponent system which comprises at least two separate components, wherein the first component comprises a composition as claimed in claim 11 and the second component comprises a protic compound.

16. The multicomponent system as claimed in claim 15, wherein the protic compound is an aqueous component and the aqueous component has a pH of 4.0 to 9.5.

17. The multicomponent system as claimed in claim 16, wherein the aqueous component has a pH of 5.0 to 6.5.

18. The multicomponent system as claimed in claim 16, wherein the aqueous component comprises or consists of a polyurethane dispersion.

19. The α-alkoxysilane-terminated prepolymer as claimed in claim 1, wherein the polyisocyanate is hexamethylene 1,6 diisocyanate.

* * * * *